United States Patent [19]
Nitobe et al.

[11] Patent Number: 5,872,266
[45] Date of Patent: Feb. 16, 1999

[54] PROCESS FOR PRODUCING 3-METHYLTETRAHYDROFURAN

[75] Inventors: Hiroyuki Nitobe; Masaki Takemoto; Takafumi Abe, all of Niigata-ken, Japan

[73] Assignee: Mitsubishi Gas Chemical Co., Inc., Tokyo, Japan

[21] Appl. No.: 925,027

[22] Filed: Sep. 8, 1997

[30] Foreign Application Priority Data

Sep. 27, 1996 [JP] Japan ................................ 8-256227

[51] Int. Cl.$^6$ ...................... C07D 307/00; C07D 307/02
[52] U.S. Cl. ........................................... 549/429; 549/506
[58] Field of Search ..................................... 549/429, 506

[56] References Cited

U.S. PATENT DOCUMENTS

| | | | |
|---|---|---|---|
| 4,912,236 | 3/1990 | Palm et al. | 549/429 |
| 5,391,771 | 2/1995 | Weyer et al. | 549/326 |
| 5,536,854 | 7/1996 | Weyer et al. | 549/508 |
| 5,559,254 | 9/1996 | Krug et al. | 549/429 |

FOREIGN PATENT DOCUMENTS

| | | |
|---|---|---|
| 0 589 314 A1 | 3/1994 | European Pat. Off. . |
| 0 727 422 A1 | 8/1996 | European Pat. Off. . |

*Primary Examiner*—Amelia Owens
*Attorney, Agent, or Firm*—Frishauf, Holtz, Goodman, Langer & Chick, P.C.

[57] ABSTRACT

There is disclosed a process for producing 3-methyltetrahydrofuran substantially free from any of an alcohol and water which comprises adding an organic solvent capable of forming an azeotropic mixture with an alcohol with an alkyl group having 1 to 3 carbon atoms to a mixed liquid containing 3-methyltetrahydrofuran, the alcohol and/or water as the principal components and, as the case may be, another substance, and distilling the resultant mixture of the mixed liquid and said organic solvent. According to the above process, it is made possible to efficiently separate a mixture of 3-methyltetrahydrofuran and an alcohol and/or water which mixture is difficult to separate with conventional distillation process alone, thereby efficiently producing the objective 3-methyltetrahydrofuran substantially free from any of an alcohol and water.

12 Claims, 2 Drawing Sheets

PROCESS FOR PRODUCING 3-METHYLTETRAHYDROFURAN

BACKGROUND OF THE INVENTION

1. Field of the Invention

The present invention relates to a process for producing 3-methyltetrahydrofuran. More particularly, it pertains to a process for producing 3-methyltetrahydrofuran which comprises distilling a mixed liquid containing 3-methyltetrahydrofuran and water and/or a specific alcohol as the principal components by adding an organic solvent to said mixed liquid to produce the objective 3-methyltetrahydrofuran substantially free from any of said alcohol and water.

2. Description of the Related Arts

3-Methyltetrahydrofuran is an extremely useful substance which is utilized as a comonomer for modifying poly (tetramethylene ether glycol) that is obtained by polymerizing tetrahydrofuran. (Refer to Japanese Patent Application Laid-Open No. 235320/1988 (Sho 63) and European Patent Application Laid-Open No. 343985.)

Various proposals have been made on the process for producing 3-methyltetrahydrofuran. For example, Japanese Patent Application Laid-Open No. 219981/1994 (Hei 6) describes the process for producing 2-methl-1,4-butanediol and 3-methyltetrahydrofuran by the hydrogenation of itaconic acid ester or 3-formyl-2-methylpropionic acid ester and also Japanese Patent Application Laid-Open No. 217768/1996 (Hei 8) describes the process for producing 3-methyltetrahydrofuran by the hydrogenation of methylsuccinic acid ester. However, when an attempt is made to produce 3-methyltetrahydrofuran by the use of the above-mentioned ester as a starting raw material, it is inevitable that the reaction product contains an alcohol as well as the objective 3-methyltetrahydrofuran. It is impossible to separate the 3-methyltetrahydrofuran from the alcohol by means of conventional distillation only, since it forms an azeotropic mixture with most of lower alcohols, for example, with methanol, forming an azeotrope having an azeotropic point of 64.5° C. and an azeotropic composition consisting of 25% by weight of 3-methyltetrahydrofuran and 75% by weight of methanol.

In addition, Japanese Patent Publication Nos. 9464/1974, 38264/1974 and 1038/1975 each describe the process for producing 3-methyltetrahydrofuran by the hydrogenation of 2-methyl-butyrolactone. There is described, in J.Prakt.Chem 1972, 314(5–6), 840.,Ger.Offen.2236734, the process for producing 3-methyltetrahydrofuran by the cyclization dehydration reaction of 2-methyl-1,4-butanediol. However, when an attempt is made to produce 3-methyltetrahydrofuran by using the aforesaid starting raw material, it is inevitable that the reaction product contains water as well as the objevtive 3-methyltetrahydrofuran. It is impossible, as is the foregoing case, to separate the 3-methyltetrahydrofuran from the water by means of conventional distillation only, since it forms an azeotropic mixture with water, that is, an azeotrope having an azeotropic point of 75.8° C. and an azeotropic composition consisting of 75% by weight of 3-methyltetrahydrofuran and 25% by weight of water.

On the other hand, consideration may be given to a process not in reliance on distillation, for example, a process in which the alcohol is washed away with water or a concentrated aqueous solution of caustic soda. However, the above-mentioned process can not be said to be efficient in separating the alcohol, since 3-methyltetrahydrofuran is inevitably lost to a certain extent by its being dissolved in the washing water and by the polymerization of itself.

SUMMARY OF THE INVENTION

A general object of the present invention is to provide a process for producing 3-methyltetrahydrofuran substantially free from any of an alcohol and water by efficiently separating an alcohol and water from 3-methyltetrahydrofuran which is difficult to separate therefrom by conventional distillation only.

Other objects of the present invention will be obvious from the contents of the specification hereinafter disclosed.

In the light of such actual circumstances, intensive research and investigation were made by the present inventors to achieve the above-mentioned objects. As a result, it has been found that an alcohol and/or water can be separated from 3-methyltertrahydrofuran which is difficult to separate therefrom by conventional distillation only, by adding a specific organic solvent to a mixture containing 3-methyltetrahydrofuran and a specific alcohol and/or water to form an azeotropic mixture of said organic solvent and said alcohol and/or water.

The present invention has been accomplished by the above-mentioned finding and information. Specifically, the present invention provides (1) a process for producing 3-methyltetrahydrofuran substantially free from an alcohol which comprises adding an organic solvent capable of forming an azeotropic mixture with an alcohol with an alkyl group having 1 to 3 carbon atoms to a mixed liquid containing 3-methyltetrahydrofuran and said alcohol as the principal components, and as the case may be, another substance, and distilling the resultant mixture of said mixed liquid and said organic solvent;

(2) a process for producing 3-methyltetrahydrofuran substantially free from any of an alcohol and water which comprises adding an organic solvent capable of forming an azeotropic mixture with an alcohol with an alkyl group having 1 to 3 carbon atoms and water to a mixed liquid containing 3-methyltetrahydrofuran, said alcohol and water as the principal components, and as the case may be, another substance, distilling the resultant mixture of said mixed liquid and said organic solvent, and distilling out an azeotropic mixture of said alcohol, water and said organic solvent;

(3) a process for producing 3-methyltetrahydrofuran substantially free from water which comprises adding an organic solvent capable of forming an azeotropic mixture with water to a mixed liquid containing 3-methyltetrahydrofuran and water as the principal components, and as the case may be, another substance, distilling the resultant mixture of said mixed liquid and said organic solvent, and distilling out an azeotropic mixture of water and said organic solvent. Further the present invention provides a process for producing 3-methyltetrahydrofuran which can be further efficiently put into practice by carrying out the distillation separation by the use of a distillation tower, recovering from the bottom thereof, the objective 3-methyltetrehydrofuran substantially free from any of an alcohol and water and distilling out from the top thereof, an azeotropic mixture of an alcohol and/or water and an organic solvent.

In carrying out the present invention, the use of an organic solvent which is poorly soluble in the alcohol and water can facilitate the recovery of said organic solvent through a method, for example, binary layer separation method. In addition, when a distillation tower is used for distillation, the loss of an organic solvent can be minimized by separating, through a binary layer separation method or the like, the alcohol and/or water from an azeotropic mixture which is distilled out from the top of the distillation tower and contains the alcohol and/or water and the organic solvent, and also by again feeding the organic solvent to the distillation tower through the top thereof or at an arbitrary stage thereof.

DESCRIPTION OF THE PREFERRED EMBODIMENTS

The organic solvent to be used in the present invention should be imparted with the following properties.
1. It should form an azeotropic mixture along with an alcohol and/or water, which mixture has an azeotropic temperature lower than that of the azetropic mixture of 3-methyltetrahydrofuran and said alcohol and/or water to the extent that the difference in the azeotropic temperature enables the separation between two azeotropic mixtures.
2. It should not form an azeotropic mixture with 3-methyltetrahydrofuran, or even if it forms an azeotropic mixture therewith, the azeotropic temperature thereof should be different from the azeotropic temperature of the azeotropic mixture with said alcohol and/or water to the extent that the difference in the azeotropic temperature enables the separation between the azeotropic mixtures.
3. It should form an azeotropic mixture along with an alcohol and/or water which mixture forms two liquid layers each having a specific gravity different from each other, thereby enabling the separation between the layers.
4. It should not cause chemical reaction with 3-methyltetrahydrofuran during the course of distillation.

As the organic solvent to used in the present invention, mention is made of aliphatic saturated hydrocarbons, aliphatic unsaturated hydrocarbons, alicyclic saturated or unsaturated hydrocarbons, aromatic hydrocarbons, organic halogenide, ethers, esters and the like. Examples of such organic solvents as satisfying the above-mentioned four requirements and being inexpensive and comparatively easily available include straight-chain or branched aliphatic saturated hydrocarbons, alicylic hydrocarbons and aromatic hydrocarbons. Particularly preferable specific examples among them include hydrocarbons each having 5 to 8 carbon atoms such as n-pentane, n-hexane, n-heptane, n-octane, cyclohexane, 2-methylpentane, 2-methylhexane, 2,2,3-trimethylbutane, methylcyclohexane and benzene.

Specific examples of the alcohol with an alkyl group having 1 to 3 carbon atoms which forms an azeotropic mixture with 3-methyltetrahydrofuran and causes a problem in separation in the invention of any of the preceding items (1) and (2), include methanol, ethanol, n-propanol and isopropanol.

Figure 1:
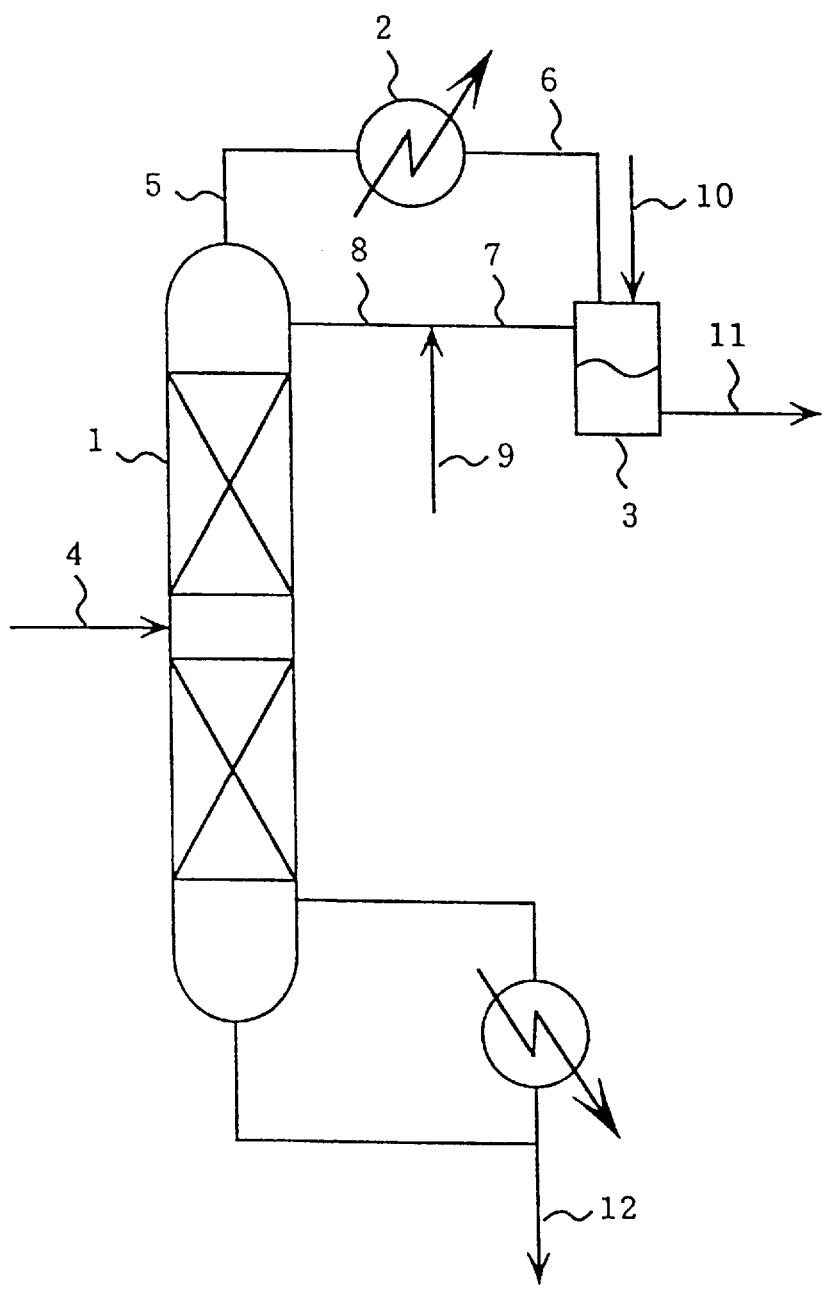
FIG. 1 is a simplified process flow diagram showing an example of process for producing 3-methyltetrahydrofuran according to the present invention, in which an alcohol and water are separated therefrom in a single distillation tower.
Figure 2:
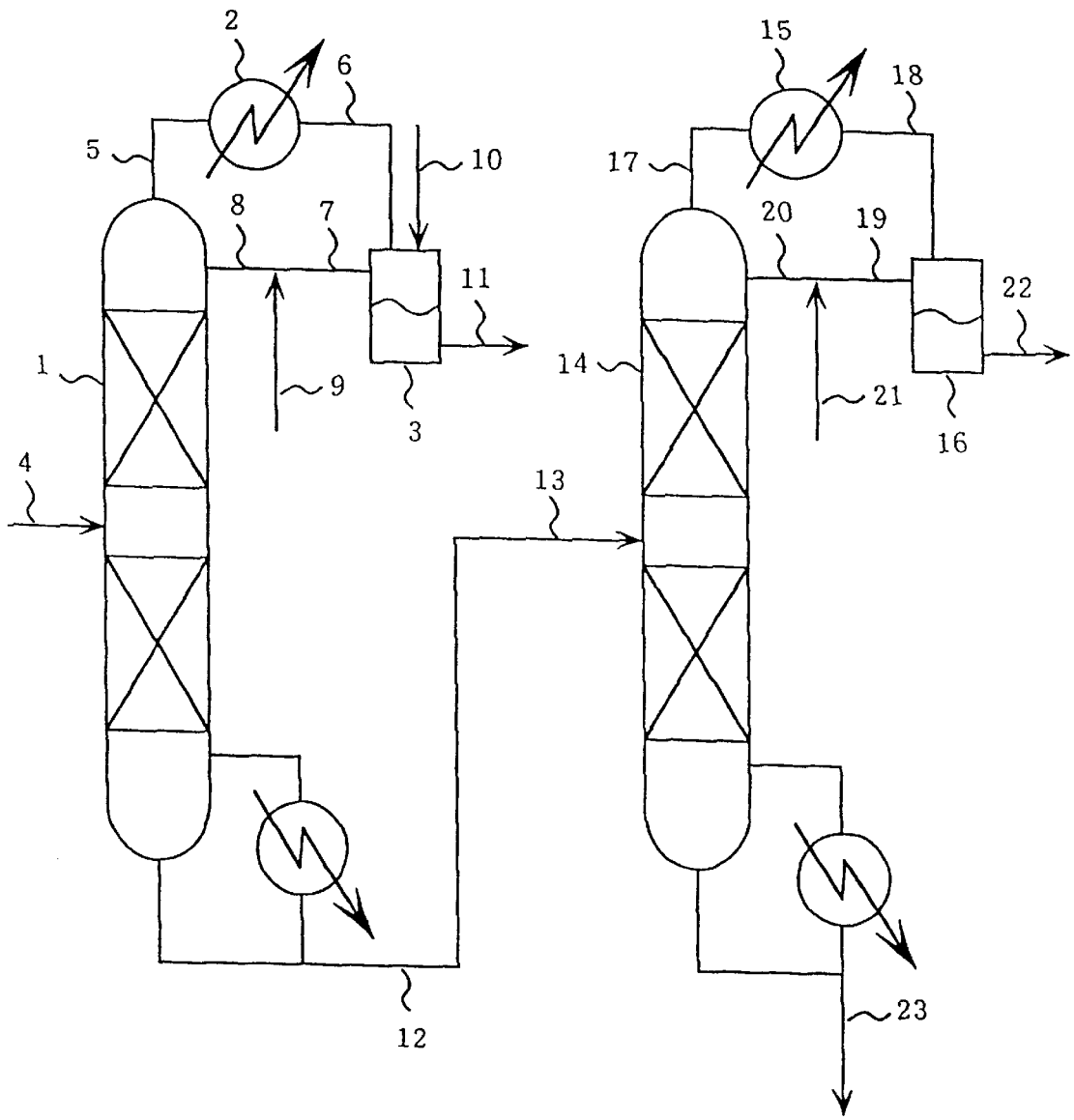
FIG. 2 is also a simplified process flow diagram showing an example of process for producing the same, in which an alcohol and water are separated therefrom in two distillation towers.

In the following, some description will be given of the embodiments of the present invention with reference to the drawings (FIG. 1 and FIG. 2). FIG. 1 points out the case where an alcohol and/or water are separated by the use of a single distillation tower, while FIG. 2 stands for the case where an alcohol and water are separated by means of two distillation towers. However, the present invention shall not be limited to the embodiment expressed in FIG. 1 or FIG. 2.

In a distillation tower 1 as shown in FIG. 1, organic solvent capable of forming an azeotropic mixture is charged in advance, and is fed, through a pipeline 4, a mixed solution containing 3-methyltetrahydrofuran, an alcohol and/or water, which is subjected to distillation therein. Thus the objective 3-methyltetrahydrofuran substantially free from alcohol and/or water is recovered from the bottom of the distillation tower 1 through a pipeline 12. On the other hand, the alcohol and/or water and an organic solvent are distilled away together forming an azeotropic mixture from the top of the distillation tower 1 through a pipeline 5 and condensed in a condenser 2. The condensed azeotropic mixture is sent from the condenser 2 through a pipeline 6 to a decanter 3, where an organic solvent layer and a (mixed) layer of the alcohol and/or water are separted from each other by means of binary layer separation. Thus the (mixed) layer of the alcohol and/or water is taken out outside the system through a pipeline 11. In the case where the layer separation fails to proceed with favorably, water or an aqueous solution of an inorganic salt is fed in the decanter 3 through a pipeline 10 in order to decrease the mutual solubility between the organic solvent and the alcohol and/or water and thereby facilitate the layer separation. As a result, the organic solvent is efficiently separated from the alcohol and/or water. Unless water is fed in the decanter 3, it sometimes happens that a part of the organic solvnet is allowed to stream outside the system by being dissolved in the (mixed) layer of the alcohol and/or water. In this case, the loss of the organic solvent can be decreased by distillating the (mixed) layer of the alcohol and/or water in another distillation tower and introducing the resultant azeotropic mixture of the organic solvent and the alcohol and/or water to the decanter 3 through the pipeline 10. On the other hand, the organic solvent layer is returned to the distillation tower 1 through a pipeline 7 and a pipeline 8. A makeup organic solvent is fed in the distillation tower 1 through a pipeline 9.

The above-described embodiment according to the present invention can be put into practice under any pressure selected from decreased to increased pressure. The cooling temperature in the decanter 3 is suitably determined in accordance with the organic solvent to be used.

According to the embodiment shown in FIG. 1 as described hereinbefore, it is made possible to efficiently separate the alcohol and water from the mixed liquid containing 3-methyltetrahydrofuran, an alcohol with an alkyl group having 1 to 3 carbon atoms and/or water as the principal components and, as the case may be, an other substance, whereby highly pure 3-methyltetrahydrofuran is efficiently produced.

It is possible, in the preceding item (2) of the invention, to recover 3-methyltetrahydrofuran substantially free from any of an alcohol and water from the bottom of the distillation tower 1 by carrying out distillation separation in a single distillation tower as described hereinbefore and distilling away an azeotropic mixture containing the alcohol, water and the organic solvent from the top thereof. In the case where one-step distillation separation is difficult depending upon the types of the organic solvent and the alcohol and the available capacity of the distillation tower to be used, it is made possible to produce 3-methyltetrahydrofuran substantially free from any of an alcohol and water by carrying out distillation separation by the use of two distillation towers, specifically by a process comprising two steps of removing, in the first distillation tower, most or all of alcohol in the form of an azeotropic mixture of the alcohol and the organic solvent; and removing, in the second distillation tower, residual alcohol and water in the form of an azeotropic mixture of water and the organic solvent.

Specifically, in the case of employing n-hexane as the organic solvent and methanol as the alcohol, when an attempt is made to remove methanol and water by continuous distillation with a single distillation tower, it must be prevented that the azeotropic mixture of 3-methyltetrahydrofuran and n-hexane be distilled away from the top of the distillation tower, said azeotropic mixture having an azeotropic point of 69.4° C. and an azeotropic composition consisting of 12% by weight of 3-methyltetrahydrofuran and 88% by weight of n-hexane. The reason for this is that in the case of the distillate being separated in two layers, 3-methyltetrahydrofuran is inevitably dissolved in the layer of methanol and water, thereby giving rise to a loss of the objective 3-methytetrahydrofuran. However, in order to prevent the azeotropic mixture of 3-methyltetrahydrofuran and n-hexane from being distilled away through the top of the distillation tower, it is made necessary to strictly control the amount of n-hexane in the distillation tower, thereby making the operation of the tower extremely difficult. There is an alternative method in which the distillation is put into practice in the presence of a somewhat excess n-hexane to prevent such difficult distillation operation. In the method, in order to prevent the azeotropic mixture of 3-methyltetrahydrofuran and n-hexane from being distilled away through the top of the distillation tower, both a highly efficient distillation tower in separation performance and a high reflux ratio are required to completely separate the azeotropic mixture of n-hexane and water from the azeotropic mixture of 3-methyltetrahydrofuran and n-hexane, the difference in azeotropic point between the two azeotropic mixtures being about 7 degrees only.

However, when the attempt is changed so as to use two distillation towers including a first distillation tower for removing most or all of the methanol and a second distillation tower for removing the residual methanol and water, the loss of 3-methyltetrahydrofuran is almost eliminated which is due to the dissolution thereof in the aqueous layer on binary layer separation of the distillate through the top of the second distillation tower, even if an azeotropic mixture of 3-methyltetrahydrofuran and n-hexane is distilled away to some extent through the top thereof. Thus, the aforestated alternative attempt enables extremely efficient implementation of the process according to the present invention.

In a distillation tower 1 in FIG. 2 showing the above-mentioned embodiment, is fed through a pipeline 4, a mixed solution containing 3-methyltetrahydrofuran, an alcohol in and water, which is subjected to distillation therein. Thus 3-methyltetrahydrofuran freed of most or all of the alcohol is recovered from the bottom of the distillation tower 1 through a pipeline 12. On the other hand, the azeotropic mixture of the alcohol and the organic solvent is distilled away from the top of the distillation tower through a pipelene 5 and condensed in a condenser 2. The condensed azeotropic mixture is sent from the condenser through a pipeline 6 to a decanter 3, where an organic solvent layer and a layer of the alcohol are separated from each other by means of binarily layering separation. Thus the layer of the alcohol is taken out outside the system through a pipeline 11. It is possible in this case to feed water in the decanter 3 through a pipeline 10 to facilitate the binary layer separation. In the case of omitting the feed of water in the decanter 3, there is sometimes used another distillation tower, where the layer of the alcohol is distilled, and an azeotropic mixture of the alcohol and the organic solvent is introduced in the decanter 3 through the pipeline 10. On the other hand, the organic solvent layer is refluxed to the distillation tower 1 through a pipeline 7 and a pipeline 8. A makeup organic solvent is fed in the distillation tower 1 through a pipeline 9. On the other hand, 3-methyltetrahydrofuran freed of most or all of the alcohol which is obtained through the bottom of the distillation tower 1 is introduced through a pipeline 13, to a distillation tower 14, where an azeotropic mixture of water and the organic solvent is distilled away, and sent through a pipeline 17, to a condenser 15, where the azeotropic mixture is condensed. The condensate is sent through a pipeline 18, to a decanter 16, where the condensate is separated into an organic solvent layer and a water layer by means of binary layer separation. Then the water layer is taken out outside the system through a pipeline 22, while the organic solvent layer is refluxed to the distillation tower 14 through a pipeline 19 and a pipeline 20. A makeup organic solvent is fed in the distillation tower 14 through a pipeline 21. In the case where the organic solvent is contained in the liquid that is sent to the distillation tower 14 through the pipeline 13, the amount of the organic solvent in the distillation tower 14 increases. In this case, however, by withdrawing a proper amount of the organic solvent through the pipeline 21, the amount of the organic solvent in the system is maintained constant at all times. THus, the objective 3-methyltetrahydrofuran substantially free from any of the alcohol and water is recovered from the bottom of the distillation tower 14 through a pipeline 23.

As described in detail hereinbefore, the process according to the present invention makes it possible to efficiently separate an alcohol and water that are present in the reaction product and difficult to separate therefrom in the production of 3-methyltetrahydrofuran.

In the following, the present invention will be descirbed in more detail with reference to working examples, which however shall not limit the present invention thereto.

EXAMPLE 1

The apparatus that was used in this example is given in FIG. 1. The specification of the distillation column used is as follows:

Upper stages: 20 mm diameter×600 mm height glass-made packed tower, packed inside with SUS316 made Dickson packings of 3 mm in size.

Lower stages: 20 mm diameter×300 mm height glass-made packed tower, packed inside with SUS316 made McMahon packings of 6 mm in size.

Working pressure: atmospheric pressure

There were used a mixed solution of 3-methyltetrahydrofuran, methanol and water as the starting material and n-hexane as the organic solvent.

The distillation tower was charged in advance, with 50 milliliter (mL) of n-hexane.

In an intermediate stage of the distillation tower was fed the mixed solution of 3-methyltetrahydrofuran, methanol and water having a composition consisting of 44.4% by weight of 3-methyltetrahydrofuran, 41.8% by weight of methanol and 13.8% by weight of water at a feed rate of 58.8 g/hour. From the bottom of the distillation tower was taken out a mixed liquid free from methanol, containing 3-methyltetrahydrofuran and water having a composition consisting of 72.9% by weight of 3-methyltetrahydrofuran, 24.7% by weight of water and 2.4% by weight of n-hexane at a discharge rate of 36.5 g/hour. An azeotropic mixture of the alcohol and the organic solvent was distilled away from the top of the distillation tower and was condensed in a cooler, and the resultant condensate was introduced in a decanter, where layering separation was carried out at 39.2° C. with a water feed rate of 29.7 g/hour. Thus, the methanol layer containing 53.9% by weight of water was taken out outside the system. The resultant distillate, flow rates of the liquids related to distillation, temperatures and chemical compositions thereof are given in Table 1.

TABLE 1

|  | Flow rate (g/hr) | Temperature (°C.) | Composition (wt. %) | | | | Number of pipeline[2] |
|---|---|---|---|---|---|---|---|
|  |  |  | methanol | 3-MT[1] | water | n-hexane |  |
| Feed to distillation tower (1) | 58.8 | 33.4 | 41.8 | 44.4 | 13.8 | — | 4 |
| Distillate from distillation tower (1) | — | 49.8 | 24.1 | 0.0 | 0.5 | 75.7 | 5 |
| Bottom from distillation tower (1) | 36.5 | 82.9 | 0.0 | 72.9 | 24.7 | 2.4 | 12 |
| Effluent from decanter (3) | 53.4 | 39.2 | 46.1 | 0.0 | 53.9 | 0.0 | 11 |
| Feed water to decanter (3) | 29.7 | — | — | — | 100.0 | — | 10 |
| Makeup organic solvent | 0.9 | — | — | — | — | 100.0 | 9 |

Remarks
[1] 3-methyltetrahydrofuran
[2] Number of pipeline in FIG. 1

EXAMPLE 2

The apparatus that was used in this example is given in FIG. 1. The specification of the distillation tower used is as follows:
Upper stages: 20 mm diameter×600 mm height glass-made packed tower, packed inside with SUS316 made Sulzer laboratory scale packings.
Lower stages: 20 mm diameter×300 mm height glass-made packed tower, packed inside with SUS316 made Dickson packings of 3 mm in size.
Working pressure: atmospheric pressure There were used a mixed solution of 3-methyltetrahydrofuran, methanol, water and m-xylene as the starting material and n-hexane as the organic solvent.

The distillation tower was charged in advance, with 50 milliliter (mL) of n-hexane.

In an intermediate stage of the distillation tower was fed the mixed solution of 3-methyltetrahydrofuran, methanol, water and m-xylene having a composition consisting of 48.0% by weight of 3-methyltetrahydrofuran, 35.7% by weight of methanol, 10.0% by weight of water and 6.3% by weight of m-xylene at a feed rate of 64.9 g/hour. From the bottom of the distillation tower was taken out a mixed liquid of 3-methyltetrahydrofuran and m-xylene having a composition consisting of 88.4% by weight of 3-methyltetrahydrofuran, 11.5% by weight of m-xylene and 210 ppm of water at a discharge rate of 35.0 g/hour. An azeotropic mixture of the methanol, water and n-hexane was distilled away from the top of the distillation tower and was condensed in a cooler, and the resultant condensate was introduced in a decanter at a temperature of 39.2° C., where layer separation was carried out with a water feed rate of 28.2 g/hour. Thus, the methanol/water layer (39.8% by weight of methanol and 60.1% by weight of water) was taken out outside the system. The resultant distillate, flow rates of the liquids related to distillation, temperatures and chemical compositions thereof are given in Table 2.

TABLE 2

|  | Flow rate (g/hr) | Temperature (°C.) | Composition (wt. %) | | | | |
|---|---|---|---|---|---|---|---|
|  |  |  | methanol | 3-MT[1] | water | n-hexane | m-xylene |
| Feed to distillation tower (1) | 64.9 | 30.5 | 35.7 | 48.0 | 10.0 | 0.0 | 6.3 |
| Distillate from distillation tower (1) | — | 57.2 | 11.7 | 0.0 | 3.3 | 85.0 | 0.0 |
| Bottom from distillation tower (1) | 35.0 | 94.0 | 0.0 | 88.4 | 210 ppm | 0.0 | 11.5 |
| Effluent from decanter (3) | 58.2 | 39.2 | 39.8 | 0.0 | 60.1 | 0.0 | 0.0 |
| Feed water to decanter (3) | 28.2 | — | 0.0 | 0.0 | 100.0 | 0.0 | 0.0 |

Remarks
[1] 3-methyltetrahydrofuran

EXAMPLE 3

The apparatus that was used in this example is given in FIG. 2. The specification of the distillation towers used is as follows:

Distillation tower No. 1: Identical with distillation tower No. 2.
Upper stages: 20 mm diameter×600 mm height glass-made packed tower, packed inside with SUS316 made Dickson packings of 3 mm in size.
Lower stages: 20 mm diameter×300 mm height glass-made packed tower, packed inside with SUS316 made Dickson packings of 3 mm in size.
Working pressure: atmospheric pressure There were used a mixed solution of 3-methyltetrahydrofuran, methanol, water and m-xylene as the starting material and n-hexane as the organic solvent. The distillation tower No. 1 was charged in advance, with 50 mL of n-hexane.

In an intermediate stage of the distillation tower No. 1 (symbol 1 in FIG. 2) was fed the mixed solution of 3methyltetrahydrofuran, methanol, water and m-xylene having a composition consisting of 48.0% by weight of 3-methyltetrahydrofuran, 35.7% by weight of methanol, 10.0% by weight of water and 6.3% by weight of m-xylene at a feed rate of 62.9 g/hour. An azeotropic mixture of methanol and n-hexane was distilled away from the top of the distillation tower NO. 1 and was condensed in a cooler, and the resultant condensate was introduced in a decanter at a temperature of 36.2° C., where layer separation was carried out with a water feed rate of 29.0 g/hour. Thus, the methanol-water layer (45.1% by weight of methanol and 54.9% by weight of water) was taken out outside the system. On the other hand, from the bottom of the distillation tower No. 1 was taken out a mixed liquid almost free from methanol, containing 3-methyltetrahydrofuran, water and m-xylene having a composition consisting essentially of 70.9% by weight of 3-methyltetrahydrofuran, 0.4% by weight of methanol, 19.4% by weight of water and 9.2% by weight of m-xylene at a discharge rate of 42.4 g/hour.

In an intermediate stage of the distillation tower No. 2 (symbol 14 in FIG. 2) which had been charged in advance, with n-hexane, was fed the mixed soution of 3-methyltetrahydrofuran, water and m-xylene which had been withdrawn from the bottom of the distillation tower No. 1, having a composition consisting of 70.9% by weight of 3-methyltetrahydrofuran, 0.4% by weight of methanol, 19.4% by weight of water and 9.2% by weight of m-xylene at a feed rate of 42.4 g/hour. An azeotropic mixture of water and n-hexane was distilled away from the top of the distillation tower No. 2 and was condensed in a cooler, and the resultant condensate was introduced in a decanter at a temperature of 40.2° C., where layer separation was carried out. Thus, the water layer (2.0% by weight of methanol and 98.0% by weight of water) was taken out outside the system. On the other hand, from the bottom of the distillation tower No. 2 was taken out a mixed liquid of 3-methyltetrahydrofuran and m-xylene having a composition consisting essentially of 88.3% by weight of 3-methyltetrahydrofuran, 11.6% by weight of m-xylene and 180 ppm of water at a discharge rate of 34.0 g/hour. The resultant distillate, flow rates of the liquids related to distillation, temperautres and chemical compositions thereof are given in Table 3.

TABLE 3

|  | Flow rate (g/hr) | Temperature (°C.) | Composition (wt. %) | | | | |
| --- | --- | --- | --- | --- | --- | --- | --- |
|  |  |  | methanol | 3-MT[(1)] | water | n-hexane | m-xylene |
| Feed to distillation tower (1) | 62.9 | 35.5 | 35.7 | 48.0 | 10.0 | 0.0 | 6.3 |
| Distillate from distillation tower (1) | — | 50.1 | 26.0 | 0.0 | 0.0 | 74.0 | 0.0 |
| Bottom from distillation tower (1) | 42.4 | 82.9 | 0.4 | 70.9 | 19.4 | 0.0 | 9.2 |
| Effluent from decanter (3) | 49.4 | 36.2 | 45.1 | 0.0 | 54.9 | 0.0 | 0.0 |
| Feed water to decanter (3) | 29.0 | — | 0.0 | 0.0 | 100.0 | 0.0 | 0.0 |
| Feed to distillation tower (14) | 42.4 | 80.2 | 0.4 | 70.9 | 19.4 | 0.0 | 9.2 |
| Distillate from distillation tower (14) | — | 60.1 | 0.1 | 0.5 | 6.0 | 93.6 | 0.0 |
| Bottom from distillation tower (14) | 34.0 | 92.0 | 0.0 | 88.3 | 180 ppm | 0.0 | 11.6 |
| Effluent from decanter (16) | 8.6 | 40.2 | 2.0 | 0.0 | 98.0 | 0.0 | 0.0 |

Remarks
[(1)]3-methyltetrahydrofuran

EXAMPLE 4

In an intermediate stage of a distillation tower same as that used in Example 1, which had been charged in advance, with 50 g of n-hexane, was fed the mixed liquid of 3-methyltetrahydrofuran, water and m-xylene having a composition consisting of 71.0% by weight of 3-methyltetrahydrofuran, 19.8% by weight of water and 9.2% by weight of m-xylene at a feed rate of 40.6 g/hour, while stirring was continued with a magnetic stirrer for the mixed liquid which would have been separated into two layers unless stirred. From the bottom of the distillation tower was taken out a mixed liquid of 3-methyltetrahydrofuran and m-xylene having a composition consisting essentially 87.8% by weight of 3-methyltetrahydrofuran, 11.5% by weight of m-xylene and 150 ppm of water at a discharge rate of 32.0 g/hr. An azeotropic mixture of water and n-hexane was distilled away from the top of the distillation tower and was condensed in a cooler, and the resultant condensate was introduced in a decanter at a temperature of 32.8° C., where layer separation was carried out. Thus, the water layer was taken out outside the system, while the organic layer containing mostly of n-hexane was refluxed to the distillation tower at the top thereof. The resultant distillate, flow rates of the liquids related to distillation, temperatures and chemical compositions thereof are given in Table 4.

TABLE 4

| | Flow rate (g/hr) | Temperature (°C.) | Composition (wt. %) | | | |
|---|---|---|---|---|---|---|
| | | | 3-MT[(1)] | water | n-hexane | m-xylene |
| Feed to distillation tower (1) | 40.6 | 29.5 | 71.0 | 19.8 | 0.0 | 9.2 |
| Distillate from distillation tower (1) | — | 60.1 | 0.5 | 6.0 | 94.0 | 0.0 |
| Bottom from distillation tower (1) | 32.0 | 92.0 | 87.8 | 150 ppm | 0.0 | 11.5 |
| Effluent from decanter (3) | 8.0 | 32.8 | 0.0 | 100 | 0.0 | 0.0 |

Remarks
[(1)]3-methyltetrahydrofuran

What is claimed is:

1. A process for producing 3-methyltetrahydrofuran substantially free from an alcohol which comprises adding an organic solvent capable of forming an azeotropic mixture with an alcohol with an alkyl group having 1 to 3 carbon atoms to a mixed liquid containing 3-methyltetrahydrofuran and said alcohol, and distilling the resultant mixture of said mixed liquid and said organic solvent.

2. The process according to claim 1, wherein a specific organic solvent poorly soluble in the alcohol is added to the mixed liquid, an azeotropic mixture of the alcohol and said specific organic solvent is distilled off, cooled and condensed, and thereafter the resultant condensate is separated into the alcohol and said specific organic solvent by means of binary layer separation to recover said specific organic solvent.

3. The process according to claim 1, wherein the mixed liquid is distilled with a distillation tower, an azeotropic mixture of the alcohol and the organic solvent is distilled out through the top of said distillation tower and then separated into the alcohol and the organic solvent, which is continuously refluxed to said distillation tower.

4. A process for producing 3-methyltetrahydrofuran substantially free from any of an alcohol and water which comprises adding an organic solvent capable of forming an azeotropic mixture with an alcohol with an alkyl group having 1 to 3 carbon atoms and water to a mixed liquid containing 3-methyltetrahydrofuran, said alcohol and water, and distilling the resultant mixture of said mixed liquid and said organic solvent.

5. The process according to claim 4, wherein a specific organic solvent poorly soluble in the alcohol and water is added to the mixed liquid, an azeotropic mixture of the alcohol, water and said specific organic solvent is distilled out, cooled and condensed, and then the resultant condensate is separated into the alcohol/water and said specific organic solvent by means of binarily layering separation to recover said specific organic solvent.

6. The process according to claim 4, wherein the mixture is distilled with a distillation tower, the azeotropic mixture of the alcohol, water and the organic solvent is distilled out through the top of the distillation tower and then separated into the alcohol/water and the organic solvent, which is continuously refluxed to said distillation tower.

7. The process according to claim 4, wherein the mixed liquid is distilled with two distillation towers, most or all of the alcohol is removed in the form of an azeotropic mixture of the alcohol and the organic solvent from a mixture comprising 3-methyltetrahydrofuran in a first distillation tower and in a second distillation tower, the residual alcohol and the water are removed in the form of an azeotropic mixture of the water and the organic solvent to produce 3-methyltetrahydrofuran substantially free from any of an alcohol and water.

8. The process according to claim 1, wherein the azeotropic mixture is distilled out, condensed and sent to a separator, where said mixture is subjected to binary layer separation by adding water thereto to suppress the mutual dissolution of the alcohol and/or water and the organic solvent, and thereby decrease the loss of the organic solvent.

9. The process according to claim 4, wherein the azeotropic mixture is distilled out, condensed and sent to a separator, where said mixture is subjected to a binary layer separation by adding water thereto to suppress the mutual dissolution of the alcohol and/or water and the organic solvent, and thereby decrease the loss of the organic solvent.

10. A process for producing 3-methyltetrahydrofuran substantially free from water which comprises adding an organic solvent capable of forming an azeotropic mixture with water to a mixed liquid containing 3-methyltetrahydrofuran and water, and distilling the resultant mixture of said mixed liquid and said organic solvent.

11. The process according to claim 8, wherein a specific organic solvent poorly soluble in water is added to the mixed liquid, an azeotropic mixture of water and said specific organic solvent is distilled out, cooled and condensed, and then the resultant condensate is separated into water and said specific organic solvent by means of binary layer separation to recover said specific organic solvent.

12. The process according to claim 10, wherein the mixed liquid is distilled with a distillation tower, an azeotropic mixture of water and the organic solvent is distilled out through the top of said distillation tower and then separated into water and the organic solvent, which is refluxed to said distillation tower.

* * * * *